_United States Patent_ [19]

Fahmy et al.

[11] 4,308,274

[45] Dec. 29, 1981

[54] N-ALKYLSULFONYL-, N-ARYLSULFONYL-, AND N-AMINOSULFONYLAMINOSULFINYL-CARBAMATE ESTERS

[75] Inventors: Mohamed A. H. Fahmy; Tetsuo R. Fukuto, both of Riverside, Calif.

[73] Assignee: The Regents of the University of California, Los Angeles, Calif.

[21] Appl. No.: 26,364

[22] Filed: Apr. 2, 1979

[51] Int. Cl.$^3$ .................... A01N 43/40; C07C 143/67; C07C 125/06; C07D 211/44
[52] U.S. Cl. ........................... 424/267; 260/453 RW; 260/465 D; 260/340.9 R; 260/346.22; 560/13; 560/137; 560/135; 560/148; 560/10; 560/134; 260/340.5 R; 544/159; 546/218; 546/242; 424/282; 424/285; 424/278; 424/300; 424/321

[58] Field of Search ....... 260/346.73; 453 RW, 465 D, 260/556 R, 340.9, 346.22, 340.5 R; 560/13, 137, 135, 148, 10, 134; 544/159; 546/218, 242; 424/267, 282, 285, 278, 300, 321; 549/51, 55

[56] References Cited

U.S. PATENT DOCUMENTS 4,072,751  2/1978  D'Silva .................... 260/453 RW _Primary Examiner_—John M. Ford
_Assistant Examiner_—Robert C. Whittenbaugh
_Attorney, Agent, or Firm_—Albert M. Herzig; Edward C. Walsh; Max Geldin

[57] ABSTRACT

A novel class of chemical compounds useful as pesticides consists of N-alkylsulfonyl-, N-arylsulfonyl-, and N-aminosulfonylaminosulfinylcarbamate esters. The preparation of these compounds and their formulation to control insects are exemplified.

44 Claims, No Drawings

N-ALKYLSULFONYL-, N-ARYLSULFONYL-, AND N-AMINOSULFONYLAMINOSULFINYLCARBAMATE ESTERS

BACKGROUND OF THE INVENTION

This invention relates to the general field of pesticides, and is particularly concerned with the production of insecticides for the control of both household insects and crop insects.

U.S. Pat. No. 3,997,549 to Fukuto and Black discloses N-arylsulfenylated derivatives of benzofuranyl methylcarbamates as effective pesticides.

U.S. Pat. No. 4,006,231 to Black and Fukuto discloses N-aminosulfenylated derivatives of carbofuran as effective pesticides.

U.S. Pat. No. 4,108,991 to Fukuto and Black discloses N-aminosulfenyl derivatives of aldicarb as pesticides.

The article "Selective Toxicity of N,N'-Thiodicarbamates" by M. A. H. Fahmy, N. M. Mallipudi and T. R. Fukuto in "Agricultural and Food Chemistry", Vol. 26, No. 3, page 550, May/June, 1978, discloses a series of N-(alkyl alkylcarbamoylsulfenyl) derivatives of methylcarbamate as insecticides.

The object of the present invention is to provide another novel class of carbamates which are effective pesticides, and procedure for preparing same.

SUMMARY OF THE INVENTION

The novel carbamate ester compounds of the invention are N-alkylsulfonyl-, N-arylsulfonyl-, and N-aminosulfonylaminosulfinylcarbamate esters. The compounds are prepared by reacting an N-chlorosulfinylcarbamate ester with alkylsulfonamides, arylsulfonamides, or sulfondiamides, in a suitable organic solvent and in the presence of a hydrogen chloride acceptor such as triethylamine or pyridine.

The resulting compounds of the invention are highly effective against certain pests and insects, and have substantially reduced mammalian toxicity, e.g. as compared to other potent insecticides such as carbofuran, described in U.S. Pat. No. 3,474,191. Thus, the invention compounds, while having high toxicity toward certain pests or insects, are relatively safe to mammals.

DETAILED DESCRIPTION OF THE INVENTION AND PREFERRED EMBODIMENTS

The sulfinylcarbamate esters or compounds of the invention have the formula noted below:

(1)

where X is selected from the group consisting of

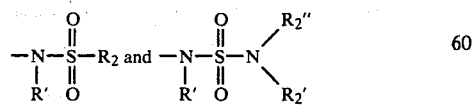

wherein R is selected from the group consisting of a hydrocarbyl group containing from 1 to 20 carbon atoms, a 5 to 6 membered heterocyclic ring containing O or S atoms and the $>C=N-$ group; $R_1$ is a hydrocarbyl group containing from 1 to 12 carbon atoms; $R'$ is an alkyl group containing from 1 to 4 carbon atoms; $R_2$ is an alkyl or aryl group, containing from 1–10 carbon atoms; $R_2'$ and $R_2''$ are alkyl groups containing from 1 to 8 carbon atoms, or $R_2'$ and $R_2''$ can be the atoms necessary to complete a 5 to 6 membered heterocyclic ring including the nitrogen atom, and which can also include O atoms, and $R_2'$ and $R_2''$ can be the same or different.

The compounds of the invention thus have the formulae (2) and (3) below:

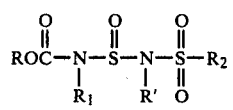 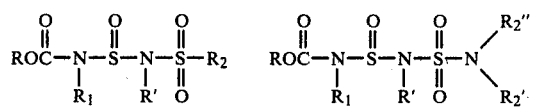

(2)    (3)

Thus, R can be a hydrocarbyl group containing only hydrogen and carbon, and containing from 1 to 20 carbon atoms, including substituted or unsubstituted alkyl, cycloalkyl, phenylalkyl and naphthylalkyl; and substituted or unsubstituted aryl, such as phenyl and naphthyl; and wherein the aforementioned groups can be substituted with one or more halogen, cyano, nitro, alkyl, alkylthio and alkoxy groups; a 5 to 6 membered heterocyclic ring containing O or S atoms, e.g. benzothienyl, furanyl, benzofuranyl and 1,3-benzodioxolyl; of the $>C=N-$ group. The latter group can be represented by the formula:

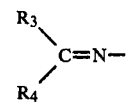

where $R_3$ is hydrogen, alkyl, alkylthio or cyano, and $R_4$ is alkyl, alkylthio, alkoxy, alkanoyl, alkoxycarbonyl, dialkylaminocarbonyl or phenyl, all of which can be unsubstituted or substituted with one or more cyano, nitro, alkylthio, alkylsulfinyl, alkylsulfonyl or alkoxy groups.

Where R is aryl, preferred examples of such aryl groups are as follows:

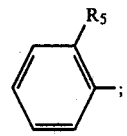

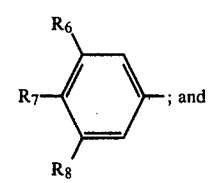
; and

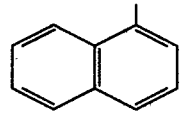

where $R_5$ is hydrogen, alkoxy, alkylthio, alkyl, alkylthioalkyl, 2-dioxalanyl or halogen, e.g. Cl or Br;

$R_6$ is alkyl, alkoxy, alkoxyalkyl or halogen;

$R_7$ is hydrogen, alkyl, halogen, alkylthio, alkoxy, dialkylamino or formyl(alkyl)amino;

$R_8$ is hydrogen, or alkyl:

and wherein the number of aliphatic carbon atoms in $R_3$, $R_4$, $R_5$, $R_6$, $R_7$, $R_8$, individually should not exceed eight:

$R_1$ is a hydrocarbyl group, either alkyl or aryl, e.g. a straight chain, branched or carbocyclic (five or six membered ring) alkyl, phenyl, phenylalkyl or naphthylalkyl, containing from 1 to 12 carbon atoms.

$R'$ is an alkyl group containing from 1 to 4 carbon atoms, e.g. methyl, ethyl, propyl, isopropyl, butyl, isobutyl or tert.butyl.

$R_2$ is alkyl or aryl, of from 1 to 10 carbon atoms. Examples of alkyl groups are methyl, ethyl, propyl, and the like. Examples of aryl groups include phenyl or substituted phenyl, where the substituents include groups such as alkyl, alkoxy or halogen, e.g. Cl or Br. Preferred substituents on the phenyl ring are 2-methyl, 4-methyl, 4-methoxy, 4-chloro and 4-fluoro.

$R_2'$ and $R_2''$ can be alkyl groups containing from 1 to 8 carbon atoms, either straight chain or branched chain, e.g. methyl, ethyl, propyl, isopropyl, butyl, isobutyl, pentyl, hexyl, isohexyl, heptyl, octyl, isooctyl, or $R_2'$ and $R_2''$ together can constitute the atoms necessary to complete a 5 to 6 membered heterocyclic ring including the nitrogen atom to which $R_2'$ and $R_2''$ are connected, such as piperidyl, and which also can include oxygen, such as morpholino.

In one group of preferred carbamate ester compounds of the invention, R is a hydrocarbyl group containing from 1 to 12 carbon atoms, either aliphatic or aromatic, including alkyl, e.g. methyl, ethyl, isopropyl, propyl, isobutyl, cycloalkyl, e.g. cyclohexyl, phenylalkyl, naphthylalkyl; aryl, e.g. phenyl, naphthyl, alkylphenyl, e.g. tolyl, xylyl, alkylnaphthyl, any of which can contain substituents such as halogen, e.g. chlorine or bromine, alkoxy, alkylthio and dialkylamino. Particularly preferred hydrocarbyl groups are alkyl, phenyl, alkylphenyl and naphthyl groups, and which can be unsubstituted or substituted, e.g. with halogen, alkoxy, dialkylamino groups, and the like, and especially wherein R is 3-alkylphenyl such as 3-isopropyl-and 3-sec-butylphenyl, 2-alkoxyphenyl such as 2-isopropoxyphenyl or 1-naphthyl. Particularly preferred also is the group of carbamate esters wherein R is a heterocyclic ring, and including fused-on heterocyclic rings, containing one or two O or S atoms, and 5 to 6 members in the heterocyclic nucleus, e.g. benzofuranyl or 1,3-benzodioxolyl, and especially a 2,3-dihydrobenzofuranyl-7 group having the formula (4) below, and the 1,3-benzodioxol-4 group having the formula (5) below:

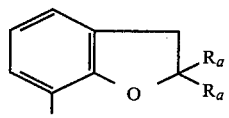 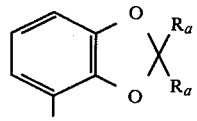

(4)       (5)

where $R_a$ is an alkyl group of 1 to about 4 carbon atoms, e.g. methyl, ethyl, propyl, n-butyl, and both $R_a$'s can be the same or different, and most preferably wherein R is the 2,3-dihydro-2,2-dimethylbenzofuranyl-7 group or the 2,2-dimethyl-1,3-benzodioxol-4 group. Another particularly preferred class of carbamates of the invention are those wherein R is a group containing the $>C=N-$ radical, as defined above. Such $>C=N-$ groups can be, for example, the following:

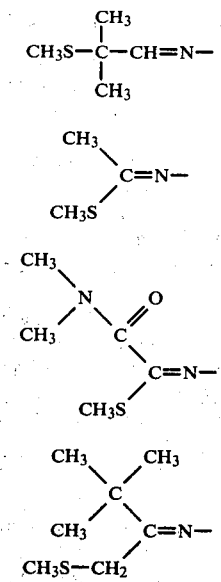

$R_1$ and $R'$ in the above preferred compounds is an alkyl group of 1 to 4 carbon atoms, preferably methyl.

$R_2$ in the above preferred compounds is an alkyl, phenyl or alkylphenyl group, of from 1–10 carbon atoms. A preferred alkyl group is methyl, and a preferred alkylphenyl group is tolyl.

$R_2'$ and $R_2''$ in the above preferred compounds are alkyl groups containing from 1 to 4 carbon atoms, and $R_2'$ and $R_2''$ can be the same or different, or $R_2'$ and $R_2''$ together can constitute the atoms necessary to complete a 5 to 6 membered nitrogen-containing heterocyclic ring, and which can include O hetero atoms, particularly the morpholino group.

The carbamate esters of the invention can be prepared by the reaction of N-chlorosulfinylcarbamate esters with sulfonamides to yield the carbamate esters of formula (2) above, or with sulfondiamides to yield carbamate esters of formula (3) above as illustrated by the following equations:

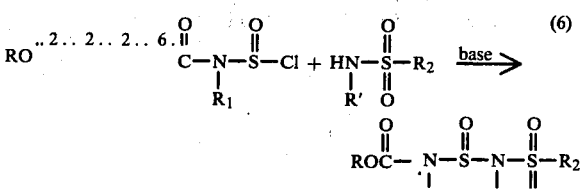

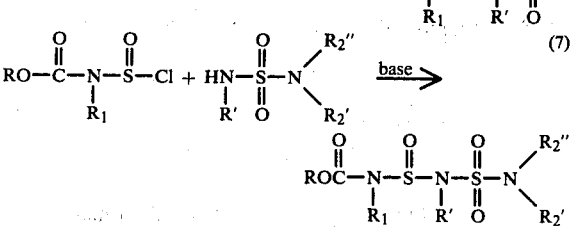

The N-chlorosulfinylcarbamate ester starting material is formed by the reaction of the corresponding carbamate with thionyl chloride, preferably using pyridine as hydrogen chloride acceptor in an inactive polar solvent such as tetrahydrofuran. Non-polar solvents such as hexane also may be used. Such ester can be formed in high yield using essentially equivalent quantities of the carbamate and thionyl chloride and slightly more than an equivalent amount of pyridine. These novel intermediates are described in the copending application Ser. No. 18,416, filed Mar. 7, 1979, by M. A. H. Fahmy and T. R. Fukuto.

Without isolation, the N-chlorosulfinylcarbamate ester intermediates can react in situ with alkylsulfonamides, arylsulfonamides or sulfondiamides according to equations (6) and (7) above. However, if desired, the N-chlorosulfinylcarbamate ester starting material in reactions (6) and (7) above can be initially prepared and isolated as an intermediate compound, and such compound then reacted with the appropriate alkylsulfonamide, arylsulfonamide, or sulfondiamide, as noted in the above reaction schemes.

In reactions (6) and (7) above, various bases can be used as HCl acceptors, such as pyridine and triethylamine. However, in the case of pyridine as a base, a longer reaction time usually is required to complete the reaction, in most instances.

The reaction temperature for reactions (6) and (7) above can range from 0° to about 50° C., according to the reactivity of the alkylsulfonamide, arylsulfonamide or the sulfondiamide. It was found however that low temperatures are necessary with triethylamine as a base, and room temperature or higher are usually employed with pyridine. The above reactions are generally carried out in an organic solvent such as dichloromethane or tetrahydrofuran.

The following are examples of preparation of the carbamate compounds of the invention.

COMPOUNDS OF THE GENERAL FORMULA (2)

EXAMPLE I

Synthesis of 2,3-dihydro-2,2-dimethylbenzofuranyl-7N-(N'-benzenesulfonyl-N'-methylaminosulfinyl)-N-methylcarbamate To a solution of 2,3-dihydro-2,2-dimethylbenzofuranyl-7-methylcarbamate (4.4 g, 0.02 mol) in 15 ml tetrahydrofuran, was added pyridine (2.0 g, 0.025 mol) and thionyl chloride (2.5 g, 0.021 mol). The mixture was stirred for 4 hours at room temperature.

The reaction mixture was filtered rapidly from pyridine hydrochloride. N-methylbenzenesulfonamide (3.5 g, 0.02 mol) was added and the mixture was cooled in an ice water bath. Triethylamine (2.2 g, 0.022 mol) was added dropwise while stirring. The mixture was stirred at room temperature for an additional half hour and diluted with 100 ml ether. The ether solution was washed with water three times (30 ml each) and then dried over anhydrous sodium sulfate.

Ether was evaporated under vacuum and the residue was subjected to high vacuum for 2 hours. A sample of the product was purified by thin layer chromatography using ethyl acetate-hexane mixture (1:3) as the developing solvent.

NMR of the purified product in chloroform-d-TMS showed the following absorptions: $\delta 8.0$–6.6 (m, 8H, aryl protons) 3.0 (s, 2H, benzylic $CH_2$), 2.9 and 2.85 (two singlets, 3H each, $CONCH_3$ and $SO_2NCH_3$), 1.5 (s, 6H, gem-di $CH_3$).

EXAMPLE II

Synthesis of 2-isopropoxyphenyl N-(N'-benzenesulfonyl-N'-methylaminosulfinyl)-N-methylcarbamate To a solution of 2-isopropoxyphenyl methylcarbamate (4.2 g, 0.02 mol) in 15 ml dry tetrahydrofuran, was added pyridine (2.0 g, 0.025 mol), and thionyl chloride (2.5 g, 0.021 mol). The mixture was stirred at room temperature for 4 hours.

The mixture was filtered rapidly and cooled in an ice-water bath. N-methylbenzenesulfonamide (3.5 g, 0.02 mol) was added and followed by triethylamine (2.2 g, 0.022 mol), added dropwise. The reaction mixture was diluted with 100 ml ether and washed with water three times (30 ml each). The ether solution was dried over anhydrous sodium sulfate and evaporated under vacuum. The residue was purified as described for example I, and the NMR spectrum of the purified sample showed the following absorptions: $\delta 8.1$–6.8 (m, 9H, aromatic protons), 4.7–4.35 (m, 1H, OCH), 3 and 2.85 (two singlets, 3H each, $CONCH_3$ and $SO_2NCH_3$), 1.35–1.25 (d, 6H, $C(CH_3)_2$).

EXAMPLE III

Synthesis of 3-isopropylphenyl N-(N'-benzenesulfonyl-N'-methylaminosulfinyl)-N-methylcarbamate To a solution of 3-isopropylphenyl methylcarbamate (3.9 g, 0.02 mol) in dry tetrahydrofuran (15 ml), was added pyridine (2.0 g, 0.025 mol) and thionyl chloride (2.5 g, 0.021 mol). The mixture was stirred at room temperature for 4 hours. Pyridine hydrochloride was filtered rapidly and N-methylbenzenesulfonamide (3.5 g, 0.02 mol) was added. The mixture was cooled in an ice-water bath and triethylamine (2.2 g, 0.022 mol) was added dropwise. After the complete addition of the amine the mixture was stirred at room temperature for an additional half hour.

Workup and purification of the final product was carried out similarly to example I.

NMR spectrum in chloroform-d-TMS gave the following absorptions: $\delta 8.1$–6.9 (m, 9H, aromatic protons), 3, 2.9 (two singlets, 3H each, $CONCH_3$), 3.2–2.7 (m, 1H, isopropyl CH), 1.3–1.2 (d, 6H, isopropyl $CH_3$).

EXAMPLE IV

Synthesis of 1-naphthyl N-(N'-benzenesulfonyl-N'-methylaminosulfinyl)-N-methylcarbamate To a solution of 1-naphthyl methylcarbamate (4.0 g, 0.02 mol) in 20 ml dry tetrahydrofuran was added pyridine (2.0 g, 0.025 mol) followed by thionyl chloride (2.5 g, 0.021 mol). The mixture was stirred at room temperature for 4 hours. Pyridine (2 g, 0.025 mol) was added and followed by 3.5 g (0.02 mol) N-methylbenzenesulfonamide and the mixture was stirred at room temperature overnight.

Workup and purification of the final product was carried out as described for example I. NMR of the final product in chloroform-d-TMS showed the following absorptions: $\delta 8.2$–7.3 (m, 12H, aromatic protons), 3.1, 2.9 (two singlets, 3H each, $CONCH_3$ and $SO_2NCH_3$).

EXAMPLE V

Synthesis of S-methyl N-[N'-(N''-benzenesulfonyl-N''-methylaminosulfinyl)-N'-methylcarbamoyloxy]thioacetimidate To a solution of S-methyl N-(methylcarbamoyloxy)-thioacetimidate (3.2 g, 0.02 mol) in 15 ml tetrahydrofuran, was added pyridine (2.0 g, 0.025 mol). The mixture was stirred and cooled in an ice-water bath. Thionyl chloride (2.5 g, 0.021 mol) was added and stirring was continued for 4 hours at room temperature.

The reaction mixture was filtered from pyridine hydrochloride and N-methylbenzenesulfonamide (3.5 g, 0.02 mol) was added and followed by triethylamine (2.2 g, 0.022 mol) added dropwise. Workup of the reaction mixture was carried out similarly to previous examples, and the residue was crystallized from benzenehexane mixture, to give 4.5 g of product, m.p. 79°–82° C.

NMR of the crystallized product in chloroform-d-TMS showed the following absorptions: $\delta$8.2–7.5 (m, 5H, aromatic protons, 2.95 and 2.9 (two singlets, 3H each, $CONCH_3$ and $SO_2NCH_3$), 2.45 (s, 3H, $N=CCH_3$), 2.3 (s, 3H, $SCH_3$).

EXAMPLE VI

Synthesis of 2,3-dihydro-2,2-dimethylbenzofuranyl-7 N-(N'-methanesulfonyl-N'-ethylaminosulfinyl)-N-methylcarbamate To a solution of 2,3-dihydro-2,2-dimethylbenzofuranyl-7-methylcarbamate (4.4 g, 0.02 mol) in 15 ml tetrahydrofuran was added pyridine (2.0 g, 0.025 mol) and thionyl chloride (2.5 g, 0.021 mol). The mixture was stirred at room temperature for 4 hours. Pyridine (2.0 g, 0.025 mol) was added and followed by N-ethylmethanesulfonamide (2.7 g, 0.022 mol) and stirring was continued overnight.

Workup and purification of the final product were carried out similarly to Example I. NMR of the purified product in chloroform-d-TMS showed the following absorptions: $\delta$7.1–6.7 (m, 3H aromatic protons, 3.75–3.55 (g, 2H, $NCH_2$), 3.15 (s, 6H, $CONCH_3$ and $SO_2CH_3$), 3.05 (s, 2H, benzylic $CH_2$), 1.5 (s, 6H, gem-di $CH_3$), 1.45–1.2 (t, 3H, $CH_3$).

EXAMPLE VII

Synthesis of 3-isopropylphenyl N-(N'-methanesulfonyl-N'-ethylaminosulfinyl)-N-methylcarbamate.

To a solution of 3-isopropylphenyl methylcarbamate (3.9 g, 0.02 mol) in 20 ml dry tetrahydrofuran, was added pyridine (1.9 g, 0.024 mol) followed by thionyl chloride (2.5 g, 0.021 mol). The mixture was stirred at room temperature for 5 hours. Pyridine (1.9 g, 0.024 mol) was added and followed by N-ethylmethanesulfonamide (2.7 g, 0.022 mol) and stirring of the reaction mixture was continued for an additional 10 hours.

Workup and purification was carried out as described for example VI.

NMR spectrum in chloroform-d-TMS showed the following absorptions: $\delta$7.4–6.9 (m, 4H, aromatic protons) 3.7–3.45 (q, 2H, $NCH_2$), 3.1 (s, 6H, $CONCH_3$ and $SO_2CH_3$), 3.2–2.7 (m, 1H, isopropyl CH), 1.5–1.1 (m, 9H, ethyl $CH_3$ and isopropyl gem-di$CH_3$).

EXAMPLE VIII

Synthesis of S-methyl N-[N'-(N''-methanesulfonyl-N''-ethylaminosulfinyl)-N'-methylcarbamoyloxy]thioacetimidate To a solution of S-methyl N-(methylcarbamoyloxy)-thioacetimidate (3.3 g, 0.02 mol) in 20 ml dry tetrahydrofuran, was added pyridine (2.0 g, 0.02 mol), and thionyl chloride (2.5 g, 0.021 mol) and the mixture was stirred at room temperature for 4 hours. The mixture was cooled in an ice-water bath and pyridine (2.0 g, 0.02 mol) was added followed by N-ethylmethanesulfonamide (2.7 g, 0.022 mol). The mixture was stirred at room temperature overnight.

Dichloromethane (100 ml) was added and the mixture was washed three times (30 ml each) with water. The dichloromethane solution was dried over anhydrous sodium sulfate and evaporated under vacuum. The residue was crystallized from dichloromethane-ether mixture to give 3.5 g of product m.p. 125°–127° C.

NMR of product in chloroform-d-TMS showed the following absorptions: $\delta$3.7–3.45 (q, 2H, $NCH_2$), 3.2 (s, 3H, $CONCH_3$), 3.05 (s, 3H, $SO_2CH_3$), 2.45 (s, 3H, $N=CCH_3$), 2.3 (s, 3H, $SCH_3$) 1.4–1.2 (t, 3H, ethyl-$CH_3$).

COMPOUNDS OF THE GENERAL FORMULA (3)

EXAMPLE IX

2,3-dihydro-2,2-dimethylbenzofuranyl-7 N-(N'-dibutylaminosulfonyl-N'-methylaminosulfinyl)-N-methylcarbamate Methylisocyanate (24.0 g, 0.42 mol) was added dropwise to a cooled mixture of 40 gm 20% fuming sulfuric acid in 100 ml nitromethane. After the complete addition of the isocyanate, the resulting suspension was refluxed for 10 minutes. The mixture was filtered and the collected crystalline methylsulfamic acid was washed with ether and air dried to give 34.5 g of the dry acid (74% yield).

Methylsulfamic acid (33 g, 0.3 mol) was mixed with 62.5 g $PCl_5$ in 100 ml benzene. The mixture was heated gently until gas evolution occurred. The heat source was removed and the reaction continued spontaneously at room temperature. After most of the solids were dissolved the mixture was refluxed with stirring for a half hour. Evaporation of the solvent and distillation of the residue under vacuum gave 32 g of methylsulfamyl chloride b.p. 90°–92° C./6.5 mm (82% yield).

Methylsulfamyl chloride (7.2 g, 0.056 mol) was dissolved in 75 ml dry benzene. Dibutylamine (15 g, 0.116 mol) was added dropwise at 10° C. to the solution and the mixture was stirred at room temperature for 2 hours. The mixture was washed with water twice and dried over anhydrous calcium chloride. The solvent was evaporated and the residue was distilled under vacuum, to give 7.0 g of product b.p. 145°–146° C./0.1 mm, which was identified as N-methyl-N',N'-dibutylsulfondiamide by NMR spectroscopy.

2,3-Dihydro-2,2-dimethylbenzofuranyl-7 methylcarbamate (4.4 g, 0.02 mol) was dissolved in 20 ml dry tetrahydrofuran. To this solution was added pyridine (2.0 g, 0.025 mol) followed by thionyl chloride (2.5 g, 0.021 mol). The mixture was stirred at room temperature for 6 hours. Then pyridine (2.0 g, 0.025 mol) was added and followed by N-methyl-N',N'-dibutylsulfondiamide (5.0 gm, 0.023 mol). The mixture was stirred at room temperature overnight and ether (150 ml) was added. The mixture was washed with water three times (50 ml each) and the organic layer was dried over anhydrous sodium sulfate. The solvent was evaporated under vacuum and the residue was crystallized from hexane, m.p. 75°–76° C.

NMR of the product in chloroform-d-TMS showed the following absorptions: 7.15–6.7 (m, 3H, aromatic protons), 3.35–3.1 (t, 4H 2NCH$_2$), 3.1 (s, 3H, CONCH$_3$), 3.05 (s, 2H, benzylic CH$_2$), 2.9 (s, 3H, SO$_2$NCH$_3$), 1.8–1.1 (m, 8H, alkyl 4CH$_2$), 1.5 (s, 6H, gem-diCH$_3$), 1.1–0.85 (t, 6H, alkyl 2CH$_3$).

EXAMPLE X 2,3-Dihydro-2,2-dimethylbenzofuranyl-7N-[N'-(N''-morpholinosulfonyl)-N'-methylaminosulfinyl]N-methylcarbamate Methylsulfamyl chloride (14.0 g, 0.11 mol), prepared as described in Example IX, was dissolved in dry benzene (150 ml). The mixture was cooled in an ice-water bath and morpholine (18.0 g, 0.2 mol) was added dropwise with stirring. After the complete addition of the amine, stirring was continued for 2 hours at room temperature. Morpholine hydrochloride was filtered and the benzene was washed with water twice (25 ml each). The benzene solution was dried over anhydrous calcium chloride, filtered and evaporated under vacuum. The oily residue was distilled, b.p. 108°–109° C./0.08 mm, and the product identified as N-methylmorpholinosulfondiamide.

2,3-Dihydro-2,2-dimethylbenzofuranyl-7 methylcarbamate (4.4 g, 0.02 mol) was dissolved in 20 ml dry tetrahydrofuran. To this solution was added pyridine (2.0 g, 0.025 mol) followed by thionyl chloride (2.5 g, 0.021 mol). The mixture was stirred at room temperature for 5 hours. Pyridine (2.0 g, 0.025 mol) was added and followed by N-methylmorpholinosulfondiamide (4.1 g, 0.023 mol). The mixture was stirred at room temperature for 12 hours. Ether (150 ml) was added and the mixture was washed with water three times (50 ml each). The ether solution was dried over anhydrous sodium sulfate, filtered, and evaporated under vacuum. The oily residue was dissolved in hexane, filtered from a small amount of unreacted carbamate and hexane was evaporated. The oil was subjected to high vacuum and the crude oil was essentially the desired product as shown by the following NMR absorptions in chloroform-d-TMS: δ7.2–6.7 (m, 3H, aromatic protons), 3.9–3.7 (m, 4H, CH$_2$OCH$_2$), 3.6–3.0 (m, 4H, CH$_2$NCH$_2$), 3.1 (s, 3H, CONCH$_3$), 3.05 (s, 2H, benzylic-CH$_2$), 3.0 (s, 3H, SO$_2$NCH$_3$), 1.45 (s, 6H, gem-diCH$_3$).

EXAMPLE XI 2,3-Dihydro-2,2-dimethylbenzofuranyl-7-N-(N'-morpholinosulfonyl-N'-ethylaminosulfinyl)-N-methylcarbamate Ethylisocyanate (21 g, 0.3 mol) was added dropwise while cooling to a stirring mixture of thirty grams of fuming sulfuric acid in nitromethane (100 ml). The reaction conditions and workup procedures are similar to Example IX. The yield was thirty grams of ethylsulfamic acid.

Ethylsulfamyl chloride was prepared from ethyl sulfamic acid (25 g, 0.2 mol) and PCl$_5$ (42 g, 0.2 mol) by the same procedure used in Example IX for the methyl analog. The product was 22.5 of ethylsulfamyl chloride, b.p. 83°–84° C./2.5 mm.

Ethylsulfamyl chloride (14.4 g, 0.1 mol) was reacted with morpholine (18.0 g, 0.2 mol) as previously described (Example X). The product, ethylmorpholinesulfondiamide, had a boiling point of 109°–110° C./0.07 mm, and its structure was confirmed by NMR spectrum.

2,3-Dihydro-2,2-dimethylbenzofuranyl-7 methylcarbamate (4.4 g, 0.02 mol) was dissolved in 20 ml dry tetrahydrofuran. To this solution was added pyridine (2.0 g, 0.025 mol) followed by thionyl chloride (2.5 g, 0.021 mol). The mixture was stirred at room temperature for 6 hours. Pyridine (2.0 g, 0.025 mol) was added and followed by ethylmorpholinosulfondiamide (4.5 g, 0.023 mol). The mixture was stirred at room temperature overnight. The workup procedure was similar to Example X.

NMR of the product in chloroform-d-TMS showed the following absorptions: δ7.2–6.7 (m, 3H, aromatic protons), 3.9–3.6 (m, 4H, CH$_2$OCH$_2$), 3.6–3.0 (m, 6H, NCH$_2$, CH$_2$NCH$_2$), 3.1 (s, 3H, CONCH$_3$), 3.0 (s, 2H, benzylic CH$_2$), 1.5 (s, 6H, gem-diCH$_3$), 1.5–1.3 (m, 3H, N-alkyl CH$_3$).

EXAMPLE XII

S-methyl N-[N'-(N''-dibutylaminosulfonyl-N''-methylaminosulfinyl)-N'-methylcarbamoyloxy]thioacetimidate.

A solution of S-methyl N-(methylcarbamoyloxy)thioacetamidate (3.3 g, 0.02 mol), pyridine (2.0 g, 0.025 mol), thionyl chloride (2.5 g, 0.021 mol) in 20 ml anhydrous tetrahydrofuran was stirred under dry conditions at room temperature for five hours. The solution was filtered rapidly from pyridine hydrochloride and the filtrate was transferred to a reaction flask. Five g of N-methyl-N',N'-dibutylsulfondiamide (0.023 mol) was added and followed by triethylamine (2.4 g, 0.024 mol) added dropwise at water-bath temperature. The mixture was stirred for half an hour at room temperature after the complete addition of the amine. Ether (100 ml) was added and the mixture was washed with water four times (30 ml each). The organic layer was dried over anhydrous sodium sulfate and the solvent was evaporated under vacuum. The oily residue was crystallized from ether-hexane mixture to give 4.4 g of solid material (51% yield), m.p. 61°–63° C.

NMR of this product in chloroform-d-TMS showed the following absorptions: δ3.35–3.15 (t, 4H, 2NCH$_2$), 3.0 (s, 3H, CONCH$_3$), 2.9 (s, 3H, SO$_2$NCH$_3$), 2.4 (s, 3H, N=CCH$_3$), 2.3 (s, 3H, SCH$_3$), 1.8–1.1 (m, 8H, alkyl CH$_2$), 1.05–0.75 (t, 6H, alkyl CH$_3$).

The following are additional examples of the carbamate compounds of the invention:

2,3-Dihydro-2,2-dimethylbenzofuranyl-7 N-(N'-2-toluenesulfonyl-N'-methylaminosulfinyl)-N-methylcarbamate.

2,3-Dihydro-2,2-dimethylbenzofuranyl-7 N-(N'-4-toluenesulfonyl-N'-methylaminosulfinyl)-N-methylcarbamate 2,3-Dihydro-2,2-dimethylbenzofuranyl-7 N-(N'-2-toluenesulfonyl-N'-ethylaminosulfinyl)-N-methylcarbamate 3-Isopropylphenyl N-(N'-2-toluenesulfonyl-N'-methylaminosulfinyl)-N-methylcarbamate 2-Isopropoxyphenyl N-(N'-2-toluenesulfonyl-N'-ethylaminosulfinyl)-N-methylcarbamate S-Methyl N-[N'-(N''-2-toluenesulfonyl-N''-methylaminosulfinyl)-N'-methylcarbamoyloxy]thioacetimidate S-Methyl N-[N'-(N''-4-toluenesulfonyl-N''-methylaminosulfinyl)-N'-methylcarbamoyloxy]thioacetimidate S-Methyl-N-[N'-(N''-ethanesulfonyl-N''-ethylaminosulfinyl)-N'-methylcarbamoyloxy]thioacetimidate S-Methyl N-[N'-(N''-methanesulfonyl-N''-methylaminosulfinyl)-N'-methylcarbamoyloxy]thioacetimidate 3-isopropylphenyl N-(N'-methanesulfonyl-N'-methylaminosulfinyl)-N-methylcarbamate 2,2-Dimethyl-1,3-benzodioxol-4 N-(N'-diethylaminosulfonyl-N'-methylaminosulfinyl)-N-methylcarbamate 2,2-Dimethyl-1,3-benzodioxol-4 N-(N'-methanesulfonyl-N'-ethylaminosulfinyl)-N-methylcarbamate 2,3-Dihydro-2,2-dimethylbenzofuranyl-7 N-(N'-diethylaminosulfonyl-N'-methylaminosulfinyl)-N-methylcarbamate 3-Isopropylphenyl N-(N'-diethylaminosulfonyl-N'-methylaminosulfinyl)-N-methylcarbamate Particularly preferred compounds according to the invention are the following:

2,3-Dihydro-2,2-dimethylbenzofuranyl-7 N-(N'-2-toluenesulfonyl-N'-methylaminosulfinyl)-N-methylcarbamate S-Methyl N-[N'-(N''-benzenesulfonyl-N''-methylaminosulfinyl)-N'-methylcarbamoyloxy]thioacetimidate S-Methyl N-[N'-(N''-methanesulfonyl-N''-ethylaminosulfinyl)-N'-methylcarbamoyloxy]thioacetimidate 2,3-Dihydro-2,2-dimethylbenzofuranyl-7 N-(N'-dibutylaminosulfonyl-N'-methylaminosulfinyl)-N-methylcarbamate S-Methyl N-[N'-(N''-dibutylaminosulfinyl-N''-methylaminosulfinyl)-N'-methylcarbamoyloxy]thioacetimidate The insecticidal sulfinylcarbamates of the invention may be formulated with the usual carriers, including additives and extenders used in the preparation of the insecticidal compositions. Thus, the toxicants of this invention, like most insecticidal agents, are generally not applied full strength, but are incorporated with the adjuvants and carriers normally employed for facilitating the dispersion of active ingredients, recognizing the accepted fact that the formulation and mode of application of a toxicant may affect the activity of the material.

The present compounds may be made into liquid concentrates by solution or emulsification in suitable liquids such as organic solvents, and into solid concentrates by admixing with talc, clays and other known solid carriers used in the insecticide art. These concentrates are compositions containing about 5–50% toxicant and the reset inert material which includes dispersing agents, emulsifying agents, and wetting agents. The concentrates are diluted for practical application, with water or other liquid for liquid sprays or with additional solid carrier for application as a dust or granular formulation.

The concentration of the toxicant in the dilution generally used for application is normally in the range of about 2% to about 0.001%. Many variations of spraying and dusting compositions in the art may be used, by substituting a compound of this invention into the compositions known or apparent to the art.

Insecticidal compositions may be formulated and applied with other active ingredients, including other insecticides, nematicides, acaricides, fungicides, plant regulators, fertilizers, etc. In applying the chemicals, it is obvious that an effective amount and concentration of the carbamate ester compounds of the invention should be employed.

BIOLOGICAL ACTIVITY

Representative carbamate esters of the invention were tested for insecticidal activity against house flies, Musca domestica. Stock 1% concentrated solutions for each of the test compounds were made in acetone, and such solutions diluted with acetone to a concentration of 0.001–0.1%. House flies were treated topically on the notum by 1 $\mu$l of each of the diluted acetone solutions and percent mortality was counted 24 hours after application. The insects were held at a constant temperature of 60° F. Results are given in $\mu$g/g.

Mammalian toxicity was determined against Swiss white mice. The test compound was applied orally using corn oil as the carrier. Results are given as $LD_{50}$ in mg of compound per kg body weight.

The toxicological data for a number of carbamates of the invention are summarized in Table I.

The term "$LD_{50}$" represents the dose needed to kill 50% of the test animals. In interpreting the values in Table I below, the lower the value for $LD_{50}$ for house flies, the greater the insecticidal potency or toxicity of that particular compound. On the other hand, the higher the value of $LD_{50}$ for mice, the lower the mammalian toxicity or the greater is the mammalian safety of such compound.

TABLE I

Toxicity of N-alkylsulfonylamino-, N-arylsulfonylamino- and N-aminosulfonylaminosulfinylcarbamate esters to house flies and mice.

| Compound of Example | House flies $LD_{50}$ ($\mu$g/g) | Mice (oral) $LD_{50}$ (mg/kg) |
|---|---|---|
| I | 9.5 | 35 |
| II | 55 | 250 |
| III | 95 | 150 |
| IV | 450 | >500 |
| V | 17.5 | 86 |
| VI | 12.5 | 75 |
| VII | 90 | 200 |
| VIII | 25 | 250 |
| IX | 12 | 25 |
| X | 13 | — |
| XI | 10 | — |
| XII | 9 | 100 |

The relatively low values for the various compounds of the invention listed in Table I for $LD_{50}$ for house flies indicates high toxicity of the invention compounds as against such insects. Thus, for example the parent material of the compounds of Examples I, VI, IX, X and XI of Table I, carbofuran, which is 2,3-dihydro-2,2-dimethyl-7-benzofuranyl methyl carbamate, has an $LD_{50}$ value for house flies, of about 6.5. The $LD_{50}$ values for house flies of the related invention compounds of these Examples are relatively comparable, ranging from 10 to 13, thus showing comparable insecticidal toxicity of such invention compounds to the potent insecticide carbofuran. However, and of particular significance, the mammalian toxicity of the invention compounds of Examples I, VI and IX of Table I above, as indicated by their high $LD_{50}$ values ranging from 25 to 75 for mice, is low, as compared to the much higher toxicity as indicated by an LD$_{50}$ value of from about 2 to about 8, found for the parent carbamate ester insecticide, carbofuran. It is also noted that the LD$_{50}$ value of 9 for house flies for the compound of Example XII indicates high insecticidal potency of such compound, while the LD$_{50}$ value of 100 against mice for this compound is much higher than the corresponding LD$_{50}$ value of 10 found for the parent carbamate ester compound, which is the carbamate starting material in Example XII. Thus, the above Table shows that the N-alkylsulfonyl-, N-arylsulfonyl- and N-aminosulfonylaminosulfinylcarbamate esters of the invention have high insecticidal activity or potency, but have substantially reduced mammalian toxicity or substantially greater mammalian safety.

While we have described particular embodiments of the invention for purposes of illustration, it will be understood that various changes and modifications within the spirit of the invention can be made, and the invention is not to be taken as limited except by the scope of the appended claims.

What is claimed is:

1. Carbamates having pesticidal activity of the formula:

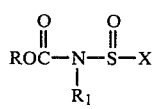

where X is selected from the group consisting of

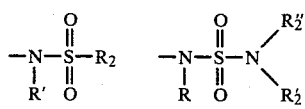

where R is selected from the group consisting of a hydrocarbyl group containing from 1 to 20 carbon atoms, a heterocyclic group selected from the class consisting of benzothienyl, furanyl, benzofuranyl and 1,3-benzodioxolyl, and the >C=N—group; R$_1$ is a hydrocarbyl group containing from 1 to 12 carbon atoms; R' is an alkyl group containing from 1 to 4 carbon atoms; R$_2$ is an alkyl or aryl group, containing from 1 to 10 carbon atoms; and R$_2'$ and R$_2''$ are alkyl groups containing from 1 to 8 carbon atoms, or R$_2'$ and R$_2''$ together with the nitrogen atom to which they are attached constitute the atoms necessary to complete a 5 to 6 membered nitrogen-containing heterocyclic ring, or morpholine, and R$_2'$ and R$_2''$ can be the same or different.

2. Carbamates having pesticidal activity selected from the class having the formulae:

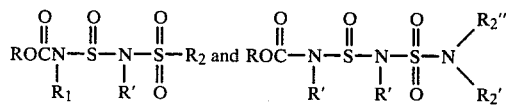

wherein R is selected from the group consisting of a hydrocarbyl group containing from 1 to 12 carbon atoms, a heterocyclic group selected from the class consisting of benzothienyl, furanyl, benzofuranyl and 1,3-benzodioxolyl, and the >C=N—group; R$_1$ and R' are alkyl groups containing from 1 to 4 carbon atoms; R$_2$ is selected from the group consisting of alkyl, phenyl and alkylphenyl, of from 1 to 10 carbon atoms; and R$_2'$ and R$_2''$ are alkyl groups containing from 1 to 4 carbon atoms, or R$_2'$ and R$_2''$ together with the nitrogen atom to which they are attached constitute the atoms necessary to complete a 5 to 6 membered nitrogen-containing heterocyclic ring, or morpholine.

3. Carbamates as defined in claim 1, wherein R$_2'$ and R$_2''$ together with the nitrogen atom to which they are attached constitute the atoms necessary to complete a 5 to 6 membered nitrogen-containing heterocyclic ring, or morpholine.

4. Carbamates as defined in claim 3, wherein R$_2'$ and R$_2''$ together with the nitrogen atom to which they are attached constitute the atoms necessary to complete a 5to 6 membered nitrogen-containing heterocyclic ring, or morpholine.

5. Carbamates as defined in claim 1, wherein R is the group

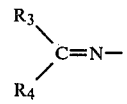

where
R$_3$ is hydrogen, alkyl, alkylthio or cyano, and
R$_4$ is alkyl, alkylthio, alkoxy, alkanolyl, alkoxycarbonyl, dialkylaminocarbonyl, or phenyl, and which can be unsubstituted or substituted with cyano, nitro, alkylthio, alkylsulfinyl, alkylsulfonyl or alkoxy groups, the number of aliphatic carbon atoms in R$_3$ and R$_4$ not exceeding eight.

6. Carbamates as defined in claim 1, wherein R is an aryl group selected from the class consisting of:

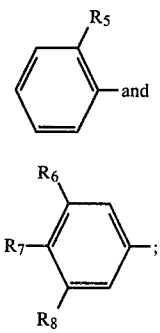

where
R$_5$ is hydrogen, alkoxy, alkylthio, alkyl, alkylthioalkyl, 2-dioxalanyl, or halogen;
R$_6$ is alkyl, alkoxy, alkoxyalkyl, or halogen;
R$_7$ is hydrogen, alkyl, halogen, alkylthio, alkoxy, dialkylamino or formyl(alkyl)amino; and
R$_8$ is hydrogen or alkyl; the number of aliphatic carbon atoms in R$_5$, R$_6$, R$_7$, and R$_8$, individually, not exceeding eight.

7. Carbamates as defined in claim 6, wherein R is:

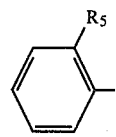

8. Carbamates as defined in claim 6, wherein R is:

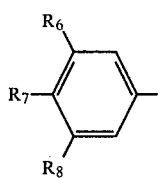

9. Carbamates as defined in claim 1, wherein R is 1-naphthyl.

10. Carbamates as defined in claim 1, where R is a heterocyclic group selected from the class consisting of benzothienyl, furanyl, benzofuranyl and 1,3-benzodioxolyl.

11. Carbamates as defined in claim 1, wherein R is benzofuranyl or 1,3-benzodioxolyl.

12. Carbamates as defined in claim 1, wherein $R_2$ is selected from the group consisting of alkyl, phenyl and alkylphenyl.

13. Carbamates as defined in claim 1, wherein $R_2'$ and $R_2''$ are alkyl groups containing 1 to 8 carbon atoms.

14. Carbamates as defined in claim 1, wherein $R_1$ is selected from the group consisting of alkyl, phenyl, phenylalkyl and naphthylalkyl.

15. Carbamates as defined in claim 2, wherein R is selected from the group consisting of alkyl, phenyl, alkylphenyl and naphthyl.

16. Carbamates as defined in claim 2, wherein R is selected from the group consisting of 3-isopropylphenyl, 3-sec.-butylphenyl, 2-isopropoxyphenyl and 1-naphthyl.

17. Carbamates as defined in claim 2, wherein R is a heterocyclic group selected from the class consisting of benzothienyl, furanyl, benzofuranyl and 1,3-benzodioxolyl.

18. Carbamates as defined in claim 17, wherein $R_2'$ and $R_2''$ are alkyl groups containing from 1 to 4 carbon atoms.

19. Carbamates as defined in claim 17, wherein $R_2$ is methyl.

20. Carbamates as defined in claim 17, wherein $R_2$ is tolyl.

21. Carbamates as defined in claim 17, wherein R is a benzofuranyl or a 1,3-benzodioxolyl group.

22. Carbamates as defined in claim 2, wherein R is selected from the class having the formulae:

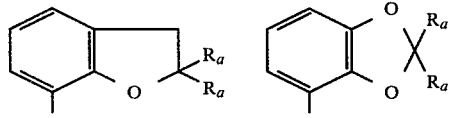

where $R_a$ is an alkyl group of 1 to about 4 carbon atoms, and both $R_a$'s can be the same or different.

23. Carbamates as defined in claim 2, wherein R is the 2,3-dihydro-2,2-dimethylbenzofuranyl-7group, or the 2,2-dimethyl-1,3-benzopdioxol-4-group.

24. Carbamates as defined in claim 23, wherein $R_2'$ and $R_2''$, together with the nitrogen atom connected to $R_2'$ and $R_2''$, constitute a piperidyl or a morpholino group.

25. Carbamates as defined in claim 23, wherein $R_2'$ and $R_2''$ are alkyl groups containing from 1 to 4 carbon atoms.

26. Carbamates as defined in claim 23, wherein $R_1$ and $R'$ are methyl.

27. Carbamates as defined in claim 2, wherein R is selected from the class having the formulae:

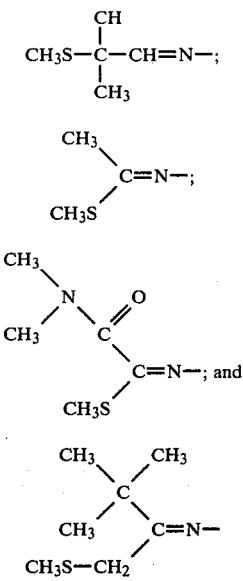

28. Carbamates as defined in claim 27, wherein $R_2'$ and $R_2''$, together with the nitrogen atom connected to $R_2'$ and $R_2''$, constitute a piperidyl or morpholino group.

29. Carbamates as defined in claim 27, wherein $R_2'$ and $R_2''$ are alkyl groups containing from 1 to 4 carbon atoms.

30. Carbamates as defined in claim 24, wherein $R_1$ and $R'$ are methyl.

31. Carbamates as defined in claim 24, wherein R is the group having the formula:

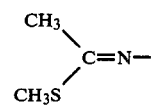

and $R_1$ and $R'$ are methyl.

32. 2,3-dihydro-2,2-dimethylbenzofuranyl-7N-(N'-2-toluene-sulfonyl-N'-methylaminosulfinyl)-N-methyl-carbamate.

33. S-methyl-N-[N'-(N''-benzenesulfonyl-N''-methylaminosulfinyl)-N'-methylcarbamoyloxy]thioacetimidate.

34. S-methyl N-[N'-(N''-methanesulfonyl-N''-ethylaminosulfinyl)-N'---methylcarbamoyloxy]thioacetimidate.

35. 2,3-dihydro-2,2-dimethylbenzofuranyl-7N-(N'-dibutylaminosulfonyl-N'-methylaminosulfinyl)-N-methylcarbamate.

36. S-methyl N-[N'-(N''-dibutylaminosulfinyl-N''-methylaminosulfinyl-N'-methylcarbamoyloxy]thioacetimidate.

37. An insecticidal composition comprising an insecticidally effective amount of a carbamate as defined in claim 1, in admixture with a carrier.

38. An insecticidal composition comprising an insecticidally effective amount of a carbamate as defined in claim 2, in admixture with a carrier.

39. An insecticidal composition comprising an insecticidally effective amount of a carbamate as defined in claim 23, in admixture with a carrier.

40. An insecticidal composition comprising an insecticidally effective amount of a carbamate as defined in claim 27, in admixture with a carrier.

41. The method of controlling insects which comprises applying to the sites of infestation an insecticidally effective amount of a compound as defined in claim 1.

42. The method of controlling insects which comprises applying to the sites of infestation an insecticidally effective amount of a compound as defined in claim 2.

43. The method of controlling insects which comprises applying to the sites of infestation an insecticidally effective amount of a compound as defined in claim 24.

44. The method of controlling insects which comprises applying to the sites of infestation an insecticidally effective amount of a compound as defined in claim 31.

* * * * *